US007981619B2

(12) United States Patent
Jeon et al.

(10) Patent No.: US 7,981,619 B2
(45) Date of Patent: *Jul. 19, 2011

(54) COMPOSITION FOR PREVENTION, TREATMENT, AND DIAGNOSIS OF CHRONIC OBSTRUCTIVE PULMONARY DISEASE (COPD)

(76) Inventors: Sook-yeong Jeon, Gyeonggi-do (KR); Dong-ho Nahm, Gyeonggi-do (KR)

( * ) Notice: Subject to any disclaimer, the term of this patent is extended or adjusted under 35 U.S.C. 154(b) by 358 days.

This patent is subject to a terminal disclaimer.

(21) Appl. No.: 11/883,589

(22) PCT Filed: Feb. 3, 2006

(86) PCT No.: PCT/KR2006/000380
§ 371 (c)(1),
(2), (4) Date: Jul. 2, 2008

(87) PCT Pub. No.: WO2006/083126
PCT Pub. Date: Aug. 10, 2006

(65) Prior Publication Data
US 2008/0299045 A1   Dec. 4, 2008

(30) Foreign Application Priority Data

Feb. 5, 2005   (KR) .................. 10-2005-0010924
Feb. 2, 2006   (KR) .................. 10-2006-0010285

(51) Int. Cl.
*G01N 33/53* (2006.01)
(52) U.S. Cl. ......................................................... 435/7.1
(58) Field of Classification Search .................. None
See application file for complete search history.

(56) References Cited

U.S. PATENT DOCUMENTS
2002/0122791 A1* 9/2002 Nicolette ................... 424/93.21
2008/0138913 A1* 6/2008 Jeon et al. ..................... 436/507

FOREIGN PATENT DOCUMENTS
WO   WO 03/023002 A2   3/2003
WO   WO 03/098211 A1   11/2003
WO   WO 2006/073254 A1   7/2006

OTHER PUBLICATIONS

Dobashi et al., Elevation of Anti-Cytokeratin 18 Antibody and Circulating Cytokeratin 18: Anti-Cytokeratin 18 Antibody Immune Complexes in Sera of Patients with Idiopathic Pulmonary Fibrosis. Lung, vol. 178, No. 3, 171-179, 2000.*
Celli BR, et al., Standards for the diagnosis and treatment of patients with COPD: a summary of the ATS/ERS position paper. Eur Respir J 2004; 23:932-46.*
Kuo et al. Identification and clinical association of anti-cytokeratin 18 autoantibody in COPD .Immunology Letters 128 (2010) 131-136.*
GenBank Accession No. AAV38219, Oct 2004, N. Kalnine et al.
Nahm et al, *American J. Respiratory Critical Care Medicine*, 165 (11);1536-1539 (2002).
Kanazawa et al, *Clinical Science*, 94:531-535 (1998).
Veeramachaneni et al, *Archives Pathology Laboratory Medicine*, 125:1494-1495 (2001).
Ryu et al, "Obstructive Lung Diseases: COPD, Asthma, and Many Imitators," *Mayo Clinic Proceedings*, vol. 76, No. 11, pp. 1144-1153, Nov. 2001.
Jeffery, "Remodeling and Inflammation of Bronchi in Asthma and Chronic Obstructive Pulmonary Disease," *Proceedings of the American Thoracic Society*, vol. 1, No. 3, pp. 176-183, 2004.
Blast Comparison of human and bovine cytokeratin 18 from Corresponding European Application No. 06 715 883.7, pp. 1-3, Oct. 22, 2009.
Chanez P., "Severe asthma is an epithelial disease", Eur Respir J, 2005, vol. 25 (6), p. 945-946.
Giallongo, Agata et al, "Molecular cloning and nucleotide sequence of a full-length cDNA for human α enolase", Proc. Natl. Acad. Sci. USA, Biochemistry 1986, vol. 83 (18), p. 6741-6745.
Global Initiative for Asthma, "Global Strategy for Asthma Management and Prevention", National Institutes of Health—National Heart, Lung and Blood Institute (NIH publication 02-3659), 2002, p. i-x, iii and 1-176.
Ishiguru et al, "Identification of *Candida albicans* Antigens Reactive with Immunoglobulin E Antibody of Human Sera", Infection and Immunity, 1992, vol. 60 (4), p. 1550-1557.
Lassalle, et al, "T and B cell immune response to a 55-kDA endothelial cell-derived antigen in severe asthma*", European Journal Immunology, 1992, vol. 23 (4), p. 796-803.
Nahm et al, "Identification of α-enolase as an autoantigen associated with severe asthma", Journal Allergy Clinical Immunology, 2006, vol. 118 (2), p. 376-381.
Nittner-Marszalska et al, "Skin prick test response to enzyme enolase of the baker's yeast (*Saccharomyces cerevisiae*) in diagnosis of respiratory allergy", Clinical Research, Med Sci Monit, 2001, 7(1), p. 121-124.
Pancholi, "Multifunctional α-enolase: its role in diseases", Cellular and Molecular Life Sciences, 2001, vol. 58 (7), p. 902-920.
Yavuz et al, "Comparative Analysis of Autoantibodies Against α-Fodrin in Serum, Tear Fluid, and Saliva from Patients with Sjögren's Syndrome", The Journal of Rheumatology, 2006, vol. 33 (7), p. 1289-1292.
Wagner et al, "Autoimmune Mechanism in Diseases of the Respiratory Tract," *Acta Allergologica*, vol. 20, pp. 1-9, 1965.
Moll et al, "The Catalog of Human Cytokeratins: Patterns of Expression in Normal Epithelia, Tumors and Cultured Cells," *Cell*, vol. 31, pp. 11-24, Nov. 1982.
O'Byrne et al, "The Many Faces of Airway Inflammation," *American Journal of Respiratory and Critical Care Medicine*, vol. 159, pp. S41-S66, 1999.

(Continued)

*Primary Examiner* — Maher M Haddad
(74) *Attorney, Agent, or Firm* — Porter Wright Morris & Arthur

(57) ABSTRACT

The present invention provides a pharmaceutical composition for preventing or treating chronic obstructive pulmonary disease (COPD) comprising cytokeratin 18 protein as an active ingredient. The present invention also provides a diagnostic composition and a diagnostic kit for diagnosing COPD comprising cytokeratin 18 protein. The present invention further provides a composition for screening a therapeutic agent for COPD, comprising one or more of cytokeratin 18 protein or autoantibodies to cytokeratin 18 obtained from patients with COPD and a method for screening a therapeutic agent for COPD using this composition. The present invention still further provides methods for diagnosing, preventing or treating COPD using cytokeratin 18 protein.

15 Claims, 3 Drawing Sheets

OTHER PUBLICATIONS

Saarloos et al, "Intermediate Filament, Laminin and Integrin Expression in Lacrimal Gland Acinar Cells: Comparison of an Immortalized Cell Line to Primary Cells, and Their Response to Retinoic Acid," *Current Eye Research*, vol. 19, No. 5, pp. 439-449, 1999.

Pauwels et al, "Global Strategy for the Diagnosis, Management, and Prevention of Chronic Obstructive Pulmonary Disease," *American Journal of Respiratory and Critical Care Medicine*, vol. 163, pp. 1256-1276, 2001.

Agusti et al, "Hypothesis: Does COPD have an Autoimmune Component?" *Thorax*, vol. 58, pp. 832-834, 2003.

Hodge et al, "Increased Airway Epithelial and T-Cell Apoptosis in COPD Remains Despite Smoking Cessation," *European Respiratory Journal*, vol. 25, No. 3, pp. 447-454, 2005.

Taraseviciene-Stewart et al, "An Animal Model of Autoimmune Emphysema," *American Journal of Respiratory Critical Care Medicine*, vol. 171, pp. 734-742, 2005.

\* cited by examiner

[Fig. 1]
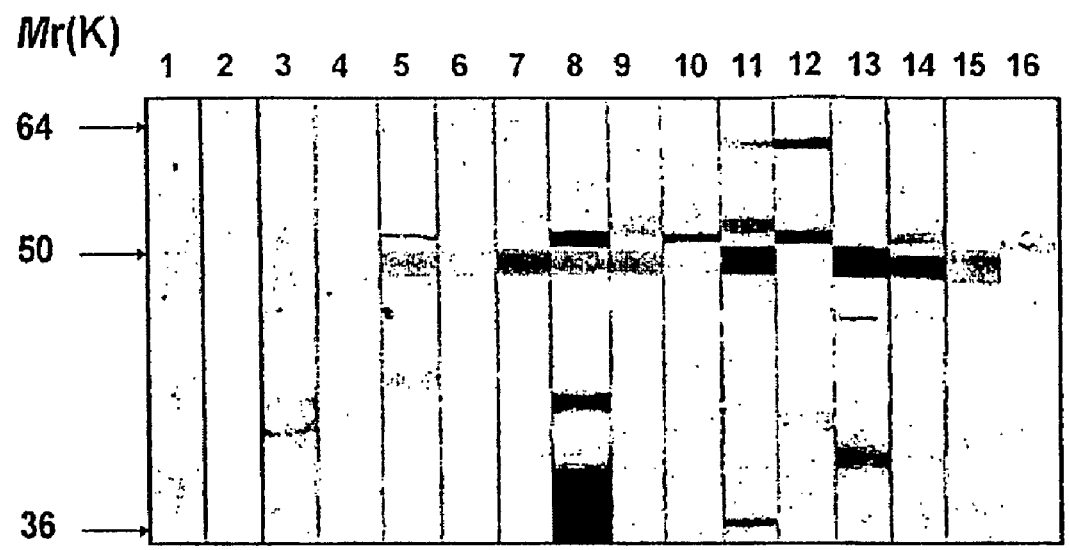
[Fig. 2]
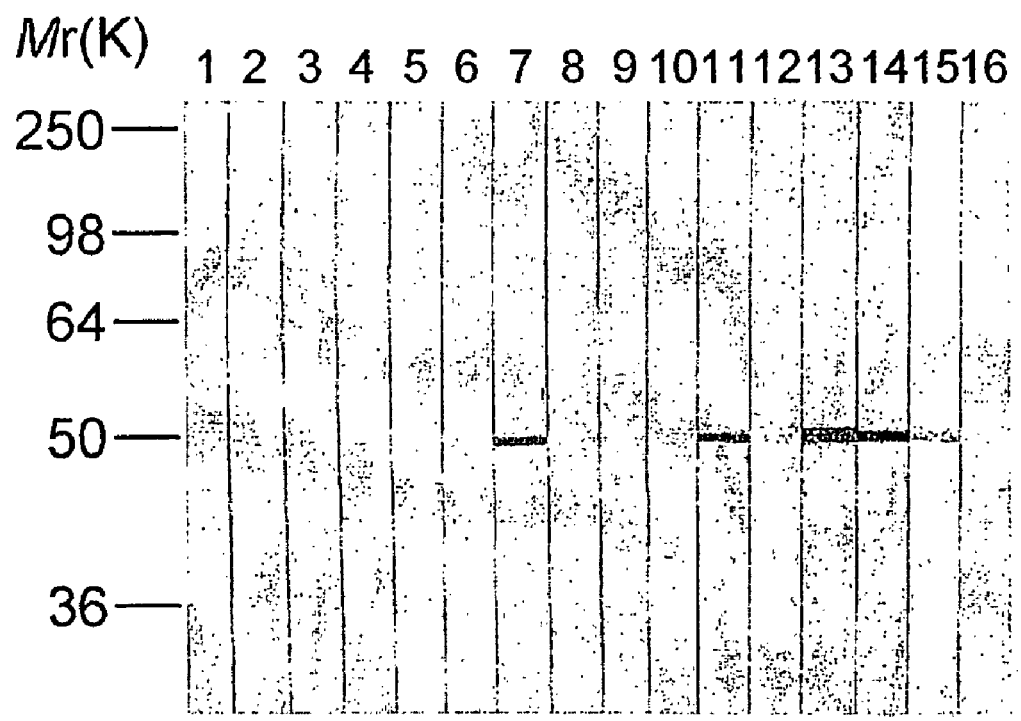

[Fig. 3]
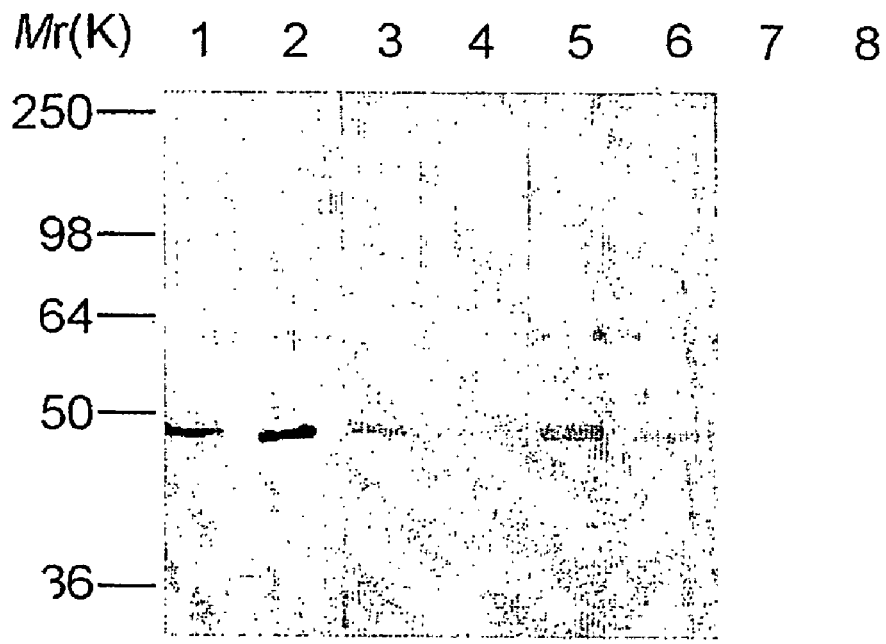
[Fig. 4]
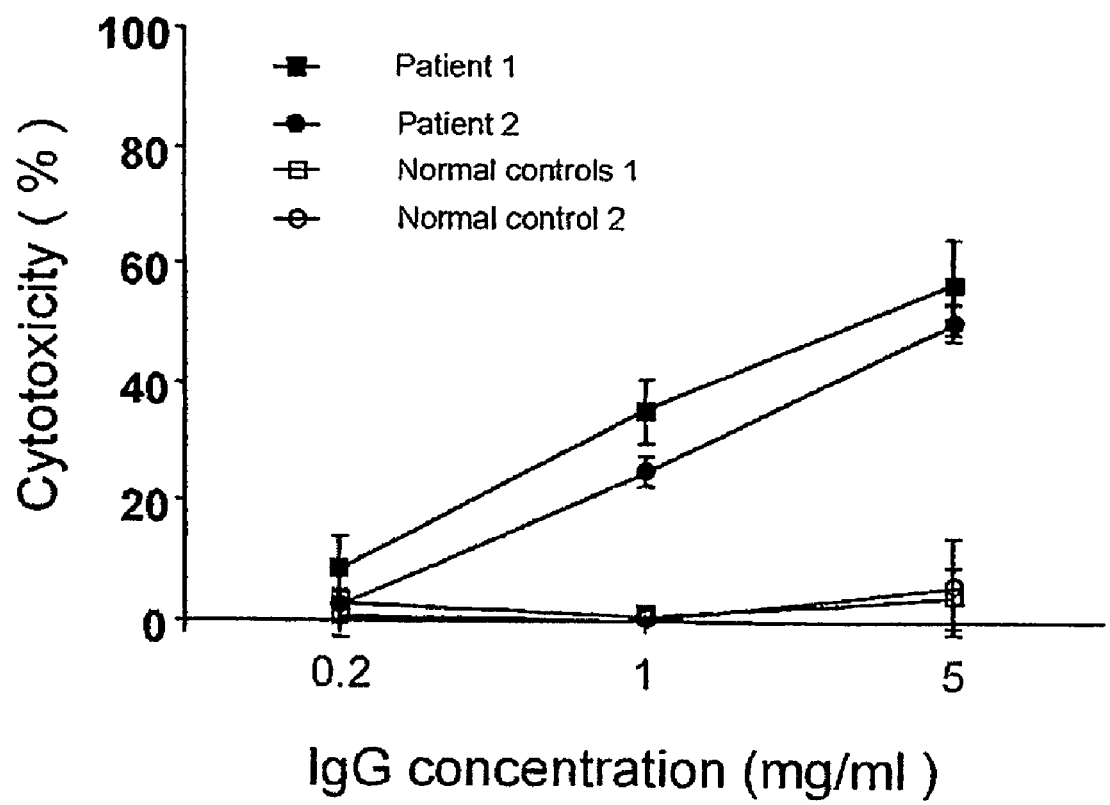

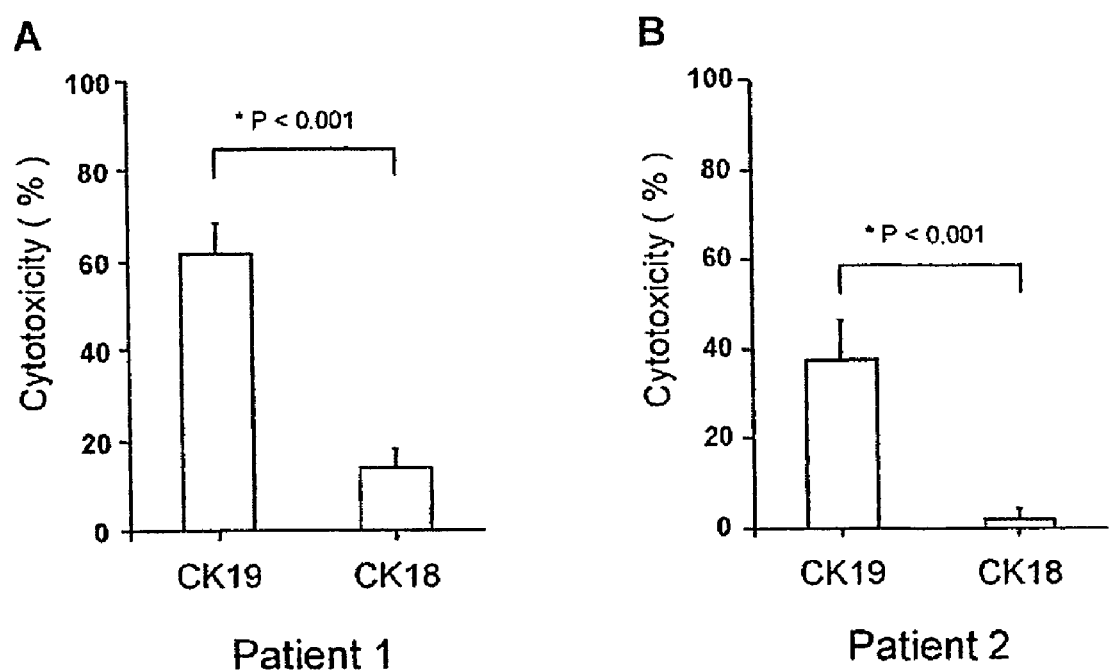
[Fig. 5]

SEQUENCE LISTING

<160> NUMBER OF SEQ ID NOS: 2

<210> SEQ ID NO 1
<211> LENGTH: 430
<212> TYPE: PRT
<213> ORGANISM: Homo sapiens

<400> SEQUENCE: 1

```
Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
        115                 120                 125

Tyr Phe Lys Ile Ile Glu Asp Leu Arg Ala Gln Ile Phe Ala Asn Thr
    130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
        195                 200                 205

Glu Leu Leu Phe Met Lys Lys Asn His Glu Glu Glu Val Lys Gly Leu
    210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255
```

-continued

Asp Glu Leu Ala Arg Lys Asn Arg Glu Glu Leu Asp Lys Tyr Trp Ser
            260                 265                 270

Gln Gln Ile Glu Glu Ser Thr Thr Val Val Thr Thr Gln Ser Ala Glu
        275                 280                 285

Val Gly Ala Ala Glu Thr Thr Leu Thr Glu Leu Arg Arg Thr Val Gln
    290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
        355                 360                 365

Ile Lys Val Lys Leu Glu Ala Glu Ile Ala Thr Tyr Arg Arg Leu Leu
    370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
            420                 425                 430

<210> SEQ ID NO 2
<211> LENGTH: 429
<212> TYPE: PRT
<213> ORGANISM: Bos taurus

<400> SEQUENCE: 2

Met Ser Phe Ser Thr Gln Ser Thr Phe Ser Asn Tyr Arg Ser Leu Gly
1               5                   10                  15

Ser Val Gln Ser Ser Gly His Arg Val Arg Pro Val Ser Ala Ala
            20                  25                  30

Ser Val Tyr Ala Gly Ala Gly Gly Ser Gly Ser Arg Ile Ser Val Ser
        35                  40                  45

Arg Thr Thr Ser Val Arg Gly Gly Trp Gly Ser Gly Asn Leu Gly Ala
    50                  55                  60

Gly Met Ala Gly Gly Leu Val Gly Val Gly Gly Ile Gln Gly Glu Lys
65                  70                  75                  80

Glu Thr Met Gln Asp Leu Asn Asp Arg Leu Ala Ser Tyr Leu Glu Lys
                85                  90                  95

Val Arg Ser Leu Glu Ala Asp Asn Arg Arg Leu Glu Ser Lys Ile Arg
            100                 105                 110

Glu His Leu Glu Lys Lys Gly Pro Gln Val Arg Asp Trp Ala His Tyr
        115                 120                 125

Leu Lys Ile Ile Glu Asp Leu Arg Ala Gln Ile Phe Ala Asn Ser Val
    130                 135                 140

Asp Asn Ala Arg Ile Val Leu Gln Ile Asp Asn Ala Arg Leu Ala Ala
145                 150                 155                 160

Asp Asp Phe Arg Val Lys Tyr Glu Thr Glu Leu Ala Met Arg Gln Ser
                165                 170                 175

Val Glu Ser Asp Ile His Gly Leu Arg Lys Val Ile Asp Asp Thr Asn
            180                 185                 190

Val Thr Arg Leu Gln Leu Glu Thr Glu Ile Glu Ala Leu Lys Glu Glu
        195                 200                 205

```
Leu Leu Phe Met Lys Lys Asn His Glu Glu Glu Val Lys Gly Leu Gln
        210             215                 220
Asn Gln Ile Ala Asn Ser Gly Leu Thr Val Glu Leu Asp Ala Pro Lys
225             230                 235                 240
Pro Gln Asp Leu Ser Lys Ile Met Ala Asp Ile Arg Ala Gln Tyr Asp
                245                 250                 255
Glu Leu Ala Gln Lys Asn Arg Glu Glu Leu Asp Lys Tyr Trp Ser Gln
                260                 265                 270
Gln Ile Glu Glu Ser Thr Thr Val Val Thr Ser Gln Thr Ala Glu Ile
            275                 280                 285
Gly Ala Ala Glu Met Thr Leu Thr Glu Leu Arg Arg Thr Val Gln Ser
        290                 295                 300
Leu Glu Ile Asp Leu Asp Ser Met Arg Asn Leu Lys Ala Ser Leu Glu
305                 310                 315                 320
Asn Ser Leu Arg Glu Val Glu Ala Arg Tyr Ala Met Gln Met Glu Gln
                325                 330                 335
Leu Asn Gly Val Leu Leu His Leu Glu Ser Glu Leu Ala Gln Thr Arg
            340                 345                 350
Ala Glu Gly Gln Arg Gln Thr Gln Glu Tyr Glu Ala Leu Leu Asn Val
            355                 360                 365
Lys Val Lys Leu Glu Ala Glu Ile Asn Thr Tyr Arg Arg Leu Leu Glu
        370                 375                 380
Asp Gly Glu Asp Phe Ser Leu Gly Asp Ala Leu Asp Ser Ser Asn Ser
385                 390                 395                 400
Arg Gln Thr Ile Gln Lys Thr Thr Thr Leu Arg Leu Val Asp Gly Lys
                405                 410                 415
Val Val Ser Glu Thr Ser Asp Thr Lys Val Leu Arg His
            420                 425
```

COMPOSITION FOR PREVENTION, TREATMENT, AND DIAGNOSIS OF CHRONIC OBSTRUCTIVE PULMONARY DISEASE (COPD)

RELATED APPLICATION

The present application is a 371 of PCT/KR2006/000380 filed Feb. 3, 2006.

BACKGROUND OF THE INVENTION

1. Technical Field

The present invention relates to compositions for prevention, treatment, and diagnosis of chronic obstructive pulmonary disease (COPD).

2. Background Art

Chronic obstructive pulmonary disease (COPD) is currently defined as chronic disease showing irreversible obstruction of airways resulting from the progression of two major underlying diseases including chronic bronchitis and pulmonary emphysema. Chronic bronchitis is defined clinically as the persistence of cough, sputum, and difficult breathing, and pulmonary emphysema is defined histopathologically as an irreversible destruction of airway walls distal to the terminal bronchiole and clinically shows slowly progressive respiratory difficulties (GOLD workshop summary, Am J Respir Crit. Care Med 2001; 163:1256-1276). Therefore, current definition of COPD excludes a bronchial asthma showing reversible obstruction of airways. COPD is currently the fourth leading cause of death in the United States and Europe, and causes of death in patients with COPD are complications of the disease such as respiratory failure or infection (GOLD workshop summary, Am J Respir Crit. Care Med 2001; 163: 1256-1276).

Currently, smoking is regarded as the most important risk factor for the development of COPD. And secretions of many inflammatory mediators (IL-8 etc.) from airway epithelial cells stimulated by smoking and other factors including air pollution or chronic infection by bacteria or virus are considered to be responsible for the development of chronic inflammation of airway tissue in COPD (GOLD workshop summary, Am J Respir Crit. Care Med 2001; 163:1256-1276). However, the reason for the chronic persistence of inflammation after acute inflammation induced by those external stimuli is not determined yet. Accordingly, it is suggested that other pathogenetic mechanisms besides smoking may be involved in the pathogenetic mechanism of COPD (O'Byrne P M, Postma D S. Am J Respir Crit. Care Med 1999; 159: S41-S66). Especially, the reasons for the persistence of airway inflammation and apoptosis of airway epithelial cells in COPD patients even after stop of smoking are not explained yet (Hodge S et al., Eur Respir J 2005; 25:447-54). The etiology and pathogenetic mechanism of COPD are not determined yet, and therefore, fundamental treatment of COPD is difficult now. The COPD patients having advanced disease and severely decreased pulmonary function are at a high risk of the disease-associated premature death (GOLD workshop summary, Am J Respir Crit. Care Med 2001; 163:1256-1276).

Currently, diagnosis of chronic obstructive pulmonary disease can be made when the patients complain of typical clinical symptoms (cough, sputum, and dyspnea, etc.) and their FEV1 measured following the inhalation of bronchodilator showed less than 80% of predictive value and the ratio of FEV1/FVC was less than 70% on pulmonary function test (GOLD workshop summary, Am J Respir Crit. Care Med 2001; 163:1256-1276). However, there is still no laboratory test which can be used for the early detection of patients with COPD who complain of typical clinical symptoms but show normal pulmonary function and thereby used for the prevention of further progression of COPD.

As a pharmacological therapy of COPD, bronchodilator and corticosteroid are known to be effective for the improvement of clinical symptoms. Direct administration of corticosteroid to the target airway tissue by inhalation devices is preferred method over systemic administration to avoid systemic side effects. Additional medications such as theophylline can also be useful. However, there is still no available therapeutic agent which can induce complete remission of COPD or fundamentally improve COPD and modify a natural course of the disease.

Detection of autoantibodies to antigens of airway or lung tissues in COPD patients has been reported (Wagner V, et al., Acta Allergol 1965; 20:1-9). Although a hypothesis that COPD is caused by autoimmune mechanism has been proposed (Agusti A, et al., Thorax 2003; 58:832-834), this hypothesis has not been clearly demonstrated because an autoantigen reacting with autoantibodies in the blood of patients with COPD has not been identified yet. Recently, it has been demonstrated that pulmonary emphysema (one of major underlying diseases causing COPD) could have been developed in animals by autoimmune response against the vascular endothelial autoantigen (Taraseviciene-Stewart L, et al., Am J Respir Crit. Care Med. 2005; 171:734-42). In the above study, it has been reported that rats immunized by antigens extracted from human vascular endothelial cells to induce autoimmune response developed pulmonary emphysema, and passive transfer of CD4+ cells from spleens of the above pulmonary emphysema-developed rats to naive rats resulted in pulmonary emphysema in recipient rats, and pulmonary emphysema has been also caused in mouse after injection of anti-endothelial cell antibodies obtained from serum of rats immunized with vascular endothelial cells (Taraseviciene-Stewart L, et al., Am J Respir Crit. Care Med. 2005; 171:734-42). This study showed that antibodies to vascular endothelial cell antigens were sufficient to trigger the development of pulmonary emphysema, although target autoantigens involved in development of the disease was not identified yet. On the basis of above, it has been suggested that autoimmune mechanism might be involved in the pathogenesis of COPD.

DISCLOSURE

Technical problem

However, previous studies could not establish a causal relationship between autoimmunity and COPD due to the lack of an identified autoantigen associated with patients with COPD and lack of a logical association between the autoantibodies in the bodily fluid of patients with COPD and the damage of airway tissue. So, autoantibody testing is not currently used for the diagnosis or classification of COPD Because the primary etiology and mechanism causing the development of COPD is not completely understood yet, a treatment method that can induce complete remission of COPD has not been developed yet. Current pharmacological therapy for COPD can improve the clinical symptoms and pulmonary function only during the continuous administration of medication, but there is no treatment method which can modify the long-term natural course of COPD or prevent a death due to COPD.

A cytokeratin 18 protein, which is identified as a target autoantigen of COPD in the present invention, is a cytoskeletal protein found primarily in epithelial cells lining the respiratory and gastrointestinal tracts, including bronchial epithelial cells and lung (alveolar) epithelial cells (Moll, R. et al., Cell 1982; 31:11-24). Although cytokeratin 18 is a predominantly intracellular protein, its strong expression on the cell surface was also observed in epithelial cells (Moll, R. et al., Cell 1982; 31:11-24; Saarloos, M. N. et al., Curr Eye Res 1999; 19:439-449). Although cytokeratin 18 protein has been also identified as a target autoantigen associated with bronchial asthma and autoimmune hepatitis (Nahm D H, et al. Am J Respir Crit. Care Med 2002; 165:1536-9), it has never been identified as a target autoantigen associated with COPD.

Technical Solution

The present inventors judged that autoantigen proteins involved in the development of COPD might be present in the airway epithelial cells on the basis of previous reports and results from deductive ratiocination of present inventors, and therefore, analyzed the airway epithelial autoantigen proteins reacting with IgG autoantibodies by immunoblot method using proteins from cultured human airway epithelial cells.

Consequently, the inventors discovered autoantibodies to airway epithelial cells in serum samples of patients with COPD, and identified that the airway epithelial autoantigen was cytokeratin 18 protein. Also, inventors demonstrated significant inhibitions of autoantibody-induced cytotoxicity of airway epithelial cells by adsorption of autoantibodies from patients with COPD with cytokeratin 18 protein, and thereby the inventors made the present invention.

It is an object of the present invention to provide a pharmaceutical composition for preventing or treating COPD comprising cytokeratin 18 protein as an active ingredient.

It is another object of the present invention to provide a diagnostic composition for diagnosing COPD comprising cytokeratin 18 protein.

It is still another object of the present invention to provide a composition for screening therapeutic agents for COPD comprising one or more of cytokeratin 18 protein, antibodies to cytokeratin 18 protein, and autoantibodies to cytokeratin 18 from patients with COPD.

The present invention provides a pharmaceutical composition for preventing or treating COPD comprising cytokeratin 18 protein as an active ingredient.

Cytokeratin 18 protein used in the present compositions for diagnosing or treating COPD, or screening therapeutic agent for COPD, can be originated from mammals including human, mouse, rat, rabbit, cow, pig, and goat.

Cytokeratin 18 protein used in the present invention can be proteins having an amino acid sequence of SEQ ID NO: 1 or an amino acid sequence of SEQ ID NO: 2, or their polypeptide fragments retaining equal physiological activity to the cytokeratin 18 proteins.

In the present invention, the above polypeptide fragments mean polypeptides retaining minimal autoantigenic epitope binding with autoantibodies from patients with COPD.

The amino acid sequence of SEQ ID NO: 1 is an amino acid sequence of human (*Homo sapiens*) cytokeratin 18 protein (NCBI accession no. P05783), and an amino acid sequence of SEQ ID NO: 2 is an amino acid sequence of bovine (*Bos taurus*) cytokeratin 18 protein (NCBI accession no. XP_582930).

Also, the cytokeratin 18 proteins can be one or more proteins selected from proteins expressed from known CDS (cDNA) sequence of a human (*Homo sapiens*) cytokeratin 18 including mRNA sequence (NCBI accession no. NM_199187) or a base sequence with polymorphism in the above nucleotide sequence.

Also, cytokeratin 18 protein can be obtained by isolating and purifying from cells or tissues of mammals, or microorganism. Or, cytokeratin 18 protein can be produced by recombinant genetic engineering technology using one of DNA base sequence encoding the amino acid sequence of SEQ ID NO: 1 or SEQ ID NO: 2 or their fragment or DNA base sequence with polymorphism in the above nucleotide sequence, thereby isolating them from cells or tissues of mammals, or microorganisms and purifying them.

The "Chronic obstructive pulmonary disease (COPD)" in the present invention includes pulmonary emphysema and chronic bronchitis.

The present invention is based on the fact identifying cytokeratin 18 protein as an airway epithelial autoantigen binding with IgG autoantibodies in the blood samples of patients with COPD, for the first time.

It can be judged from the previous reports and results of Examples in the present invention that autoantibodies in the blood of patients with COPD can directly induce cytotoxicity to airway epithelial cells through binding to cytokeratin 18 proteins of airway epithelial cells or indirectly induce cytotoxicity to airway epithelial cells and induce chronic inflammation of airway tissue through the formation of immune complexes consisted of autoantibodies and autoantigen and secondary complement activation and chemotaxis of inflammatory cells. And these damages of airway epithelial cells and chronic inflammation of airway tissue can cause clinical symptoms of COPD through the developments of irreversible structural changes of airway tissues.

In the Examples of the present invention, IgG antibodies purified from blood samples of patients with COPD induced cytotoxicity to airway epithelial cells. Also, the administration of cytokeratin 18 protein of the present invention into the model of IgG antibody-induced airway epithelial cell cytotoxicity, induced adsorptions of autoantibodies in the blood of patients with COPD, and thereby inhibited IgG antibody-induced cytotoxicity to airway epithelial cells.

Thus, the pharmaceutical composition comprising cytokeratin 18 protein of the present invention can be used as a medicament preventing, alleviating or treating COPD.

The pharmaceutical composition comprising cytokeratin 18 protein as an active ingredient may further comprise pharmaceutically and physiologically acceptable additives besides the active ingredient. Such additives may include, for example, excipients, disintergrating agents, sweeting agents, binding agents, coating agents, inflating agents, lubricants, glidants, flavoring agents, solubilizers, etc.

The pharmaceutical composition comprising cytokeratin 18 protein as an active ingredient may further comprise one or more pharmaceutically acceptable carriers to be formulated appropriately for administration.

For liquid formulation, the pharmaceutically acceptable carriers should be sterilized and suitable to living bodies. For example, the pharmaceutically acceptable carriers may include saline, sterilized water, linger solution, buffered saline, albumin injection solution, dextrose solution, malto dextrine solution, glycerin, ethanol, or the mixture of one or more of the above ingredients. If necessary, other common additives can be added, such as antioxidants, buffers, bacteriostatic agents, etc. Also, diluting agents, dispersing agents, surfactants, binders or lubricants can be further added in order to formulate the composition to injection formulations such as aqueous solution, suspension, emulsion, pills, capsules, granules, Tablets, etc. Furthermore, the present pharmaceutical composition can be appropriately formulated depending on each disease or ingredient of the composition, by using the disclosed method in Remington's Pharmaceutical Science, Mack Publishing Company, Easton Pa., as a preferable method in the art.

Formulation type of the present pharmaceutical composition comprising cytokeratin 18 protein as an active ingredient, can be granules, powder, coated tablets, tablets, capsules, suppositories, syrup, juice, suspensions, emulsions, drops, injectable liquid formulation or slowly-released formulation of active compound, etc.

The present pharmaceutical composition comprising cytokeratin 18 protein as an active ingredient, can be administered intravenously, intraarterially, intraperitoneally, intramuscularly, intrasternally, percutaneously, intranasally, rectally, orally, intraocularly, intradermally, locally, or by inhalation, according to ordinary methods.

The dosage of the present pharmaceutical composition comprising cytokeratin 18 protein as an active ingredient means an effective amount to inhibit or treat damage or inflammatory reaction of airway epithelial cells and tissues. Thus, this dosage can be modified depending on various factors such as the kind of a disease to be treated, severity of the disease, kinds and amounts of active ingredients and other ingredients contained in the composition, age, weight, general health status and sex of the patient, diet, time and route of administration, secretion rate of the composition, period of treatment, drugs used simultaneously, etc. In adults, when cytokeratin 18 proteins are administered one or several times per day, the preferable dosage of cytokeratin 18 proteins is 0.01 mg/kg~100 mg/kg.

Also, the present invention provides a method for preventing or treating COPD by administering cytokeratin 18 proteins. Preferably, the above COPD can be pulmonary emphysema or chronic bronchitis.

The present invention shows that the administration of cytokeratin 18 proteins can adsorb autoantibodies in the blood of patients with COPD thereby inhibiting autoantibody-induced cytotoxicity to airway epithelial cells and inhibiting the development of secondary inflammation of airway tissue.

The present invention provides a method of preventing or treating COPD by administering cytokeratin 18 protein. In this method, cytokeratin 18 protein can be administrated intravenously, intraarterially, intraperitoneally, intramuscular, intrasternally, percutaneously, intranasally, rectally, orally, intraocularly, intradermally, locally, or by inhalation, according to ordinary methods.

In the method of preventing or treating COPD by administering cytokeratin 18 protein, the dosage of cytokeratin 18 proteins to be administered can be referred as an effective amount to inhibit or treat autoantibody-induced cytotoxicity to airway epithelial cells or secondary inflammatory reaction of airway tissues caused by the formation of immune complex consisted of autoantigen-autoantibodies. In adults, when cytokeratin 18 proteins are administrated one or several times per day, the preferable dosage of cytokeratin 18 proteins is 0.01 mg/kg ~100 mg/kg. This dosage can be modified depending on various factors such as the kind of a disease to be treated, severity of the disease, kinds and amounts of active ingredients and other ingredients contained in the composition, age, weight, general health status and sex of the patient, diet, time or route of administration, secretion rate of composition, period of treatment, drugs used simultaneously, etc.

Also, the present invention provides the use of cytokeratin 18 protein for the manufacture of a medicament for COPD.

Further, the present invention provides a diagnostic composition comprising cytokeratin 18 protein for diagnosing COPD.

The cytokeratin 18 protein contained in the present diagnostic composition can be proteins having the amino acid sequence of SEQ ID NO: 1 or the amino acid sequence of SEQ ID NO: 2, or their polypeptide fragments retaining equal physiological activity to the cytokeratin 18 proteins, and may be originated from mammals including human, rat, mouse, rabbit, cow, pig, goat, etc.

The diagnostic composition comprising cytokeratin 18 protein according to the present invention can react with biological samples of patients with COPD, thereby showing positive results. Thus, the diagnostic composition can be used for the diagnosis of COPD.

Also, the cytokeratin 18 proteins can be one or more proteins selected from proteins expressed from known CDS (cDNA) sequence of a human (*Homo sapiens*) cytokeratin 18 including mRNA sequence (NCBI accession no. NM_199187) or a base sequence with polymorphism in the above nucleotide sequence.

Also, cytokeratin 18 protein can be obtained by isolating and purifying from cells or tissues of mammals, or microorganism. Or, cytokeratin 18 protein can be produced by recombinant genetic engineering technology using one of DNA base sequence encoding the amino acid sequence of SEQ ID NO: 1 or SEQ ID NO: 2 or their fragment or DNA base sequence with polymorphism in the above nucleotide sequence, thereby isolating them from cells or tissues of mammals, or microorganisms and purifying them.

The present diagnostic composition comprising cytokeratin 18 protein can be used for the detection, diagnosis, and classification of COPD with higher sensitivity as shown in the present Examples.

The diagnostic composition can comprise buffer or reaction solution which makes maintain physiological activity or structure of proteins, besides the proteins. Also, the diagnostic composition can be provided in the form of powder, or in the solubilized state in an appropriate buffer, or maintained at 4° C., in order to maintain stability.

The present invention provides a diagnostic kit for diagnosing COPD comprising diagnostic composition comprising cytokeratin 18 protein for diagnosing COPD.

The diagnostic kit of the present invention can comprise buffer or reaction solution which makes to maintain physiological activity or structure of proteins, besides cytokeratin 18 proteins. Further, the proteins can be provided in the form of powder, or in the solubilized state in an appropriate buffer, or maintained at 4° C., in order to maintain stability.

The diagnostic kit of the present invention can comprise components other than cytokeratin 18 protein. For the positive control result, the diagnostic kit can comprise polyclonal antibodies or monoclonal antibodies to cytokeratin 18 protein from mammals, or human's biological samples of which autoantibodies to cytokeratin 18 protein are positive. For the negative control result, the diagnostic kit can comprise other antibodies or buffers. If necessary, the diagnostic kit can further comprise other components required for the detection of autoantibodies to cytokeratin 18 protein from biological samples of subjects.

Other components required for immunodetecting reaction include anti-human IgG antibodies produced from rat, mouse, rabbit, cow, pig, or goat, etc., as the secondary antibodies, and colorizing agents, buffers, etc.

As the secondary antibodies, alkaline phosphatase (AP)-conjugated, horse radish peroxidase (HRP)-conjugated, biotin-conjugated antibodies, or fluorescent material (for example, rhodamine, Texas Red, fluorescein, phycoerythrin, etc.)-conjugated antibodies can be used.

The biotin-conjugated secondary antibodies can use AP or HRF enzyme-conjugated avidin, AP-conjugated secondary antibodies can use BCIP/NBT as color couplers, and HPR-conjugated secondary antibodies can use DAB (diaminobenzidine), etc. as color couplers, thereby inducing color reaction to determine the presence of autoantibodies. The secondary antibodies to which fluorescent materials are conjugated, can be monitored on a fluorescence microscope. Thus, from the fluorescence microscopy, the presence of autoantibodies can be determined.

The assay methods applied to the kit are known to those skilled in the art. The assay methods to be used for the kit include any techniques that can detect antigen-antibody reaction, such as fluorescence immunoassays, enzyme-substrate color reaction, enzyme immunoassays, immunoblotting, immunoprecipitation assay, antigen-antibody agglutination immunoassays, light-scattering immunoassays, radioimmunoassay, flow cytometry, complement-fixing method, etc.

The kit of the present invention can further comprise tubes, wells or plates required for mixing each component, or covering letter describing the way of using, if necessary.

The present invention provides a method for diagnosing COPD by using diagnostic compositions comprising cytokeratin 18 protein as an active ingredient.

The method comprises the following steps:
(a) obtaining biological samples of a subject suspected to have COPD;
(b) contacting the biological samples with cytokeratin 18 protein, thereby inducing the formation of immune complex; and
(c) diagnosing the COPD in the subject by detecting the immune complex, thereby determining the presence of autoantibodies to cytokeratin 18 protein.

In step (a) of the present diagnosing method, the biological samples can include any fluid which can be isolated and collected from human bodies, such as blood, plasma, serum, urine, tears, salivar, sputum, nasal secretion, bronchial secretion, bronchial washing fluid, pulmonary secretion, alveolus washing fluid, etc.

In step (b) of the present diagnosing method, the formation of immune complex can use immunoblotting, ELISA, etc., and can use any methods for detecting the antigen-antibody reaction, which are ordinary in the art.

Step (c) of the present diagnosing method is a step determining the formation of immune complex by inducing color reactions or detecting fluorescence of immune complex, and it can use any methods for detecting antigen-antibody reaction, which are ordinary in the art. If the presence of immune complex is confirmed, this result means that the subject has COPD. For the positive control result, instead of the subject's biological samples, what can be used are polyclonal antibodies or monoclonal antibodies to cytokeratin 18 protein from mammals, or human's biological samples of which autoantibodies to cytokeratin 18 protein are positive. For the negative control result, what can be used are antibodies or buffers other than the antibodies to cytokeratin 18 protein.

From the prior reports of immunological studies for other autoimmune diseases, it is known that in case of patients showing IgG autoantibodies to specific autoantigen proteins in blood, a considerable number of patients has antigen-specific T-cell reaction to the same autoantigen protein, and it is useful to test delayed type hypersensitivity after intradermal injection of the same autoantigen proteins reacting with IgG autoantibodies in the patients (Beales P E et al, Autoimmunity 2000; 32:109-113). In prior arts, skin tests of tuberculin type have been used, in which tests were performed by injecting specific antigen to subjects, intradermally, and testing the injected skin part after 24 to 72 hours of the injection to measuring the size of skin swelling (induration), thus determining the presence of delayed-type hypersensitivity reaction or late-onset skin reaction to the above antigen.

Accordingly, the diagnostic composition comprising cytokeratin 18 protein can be applied to the use of the diagnostic composition to detecting patients showing autoimmune response to cytokeratin 18 protein among patients with COPD by measuring the size of skin swelling after 24 to 72 hours of the intradermal injection of cytokeratin 18 protein.

Also, the present invention provides a method of diagnosing COPD by using a diagnostic composition comprising cytokeratin 18 protein.

The present method of diagnosing chronic COPD comprises the following steps:
a) selecting a subject suspected to have COPD;
b) injecting intradermally the diagnostic compositions comprising cytokeratin 18 protein and
c) diagnosing the COPD by examining the injected skin part after 24 to 72 hours of the injection and detecting the presence of the skin swelling and measuring the size of skin swelling, thus determining the presence of delayed-type hypersensitivity reaction or late skin reaction to cytokeratin 18 protein.

By using the present diagnostic composition and diagnosing method, the result for the presence of COPD can be obtained easily and correctly determined. Therefore, it can be used effectively for clinical study in a large scale. Also, it can be used to screen therapeutic agents or to develop treatment methods for COPD.

The present invention provides a composition for screening a therapeutic agent for COPD, comprising one or more materials of cytokeratin 18 protein, antibodies to cytokeratin 18 protein, or autoantibodies to cytokeratin 18 from the patients with COPD, and a method for screening a therapeutic agent using this composition.

Cytokeratin 18 protein contained in the present composition for screening therapeutic agents can be proteins having the amino acid sequence of SEQ ID NO: 1 or the amino acid sequence of SEQ ID NO: 2, or proteins expressed from known CDS(cDNA) sequence of a human (*Homo sapiens*) cytokeratin 18 including mRNA sequence (NCBI accession no. NM_199187) or a base sequence with polymorphism in the above nucleotide sequence, or polypeptide fragments of cytokeratin 18 protein showing equal physiological activity to cytokeratin 18 protein.

The antibodies to cytokeratin 18 protein contained in the present composition for screening therapeutic agents can be prepared for the cytokeratin 18 proteins, but it can be also obtained commonly or commercially in the art.

The compositions for screening a therapeutic agent can comprise buffer or reaction solution which makes maintain physiological activity or structure of proteins, besides cytokeratin 18 protein, antibodies to cytokeratin 18 protein, or autoantibodies to cytokeratin 18 from the patients with COPD. Also, the composition can be provided in the form of powder, or in the solubilized state in an appropriate buffer, or maintained at 4° C., in order to maintain stability.

The present compositions for screening a therapeutic agent enable the selection of a therapeutic agent for COPD, by screening the material which inhibits binding between cytokeratin 18 proteins and autoantibodies to cytokeratin 18 in the biological samples obtained from the patients with COPD, or inhibits cytotoxic reaction of the autoantibodies to cytokeratin 18 protein-expressing cells.

Also, the present invention provides a method of screening a therapeutic agent for COPD, by using compositions comprising one or more of cytokeratin 18 protein, antibodies to cytokeratin 18 protein, or autoantibodies to cytokeratin 18 from the patients with COPD, as target materials.

The method of screening a therapeutic agent for COPD comprises the following step:
(a) isolating autoantibodies from biological samples obtained from the patients with COPD;
(b) contacting test materials with the autoantibodies obtained in step (a); and
(c) selecting a therapeutic agent for COPD by determining whether the test materials can inhibit binding of the autoantibodies to cytokeratin 18 protein, or inhibit cytotoxic effects of the autoantibodies to cytokeratin 18 protein-expressing cells.

In the present method of screening a therapeutic agent, the test materials can be nucleic acids, proteins, extracts, or compounds which are expected to have possibilities of inhibitor for COPD according to ordinary selecting method, or randomly selected.

In the present method for screening a therapeutic agent, for the confirmation of the reaction between the composition for screening and the test materials, common methods used to confirm protein-protein reaction including antigen-antibody reaction or protein-compound reaction can be used.

For example, the following methods can be used: a method which reacts cytokeratin 18 proteins or autoantibodies with the test material, thereby determining the activity, yeast two-hybrid method, screening method of phage-displayed peptide clone binding to cytokeratin 18 proteins, high throughput screening (HTS) method using natural product, chemical library etc., drug hit HTS method, cell-based screening method, or screening method using DNA array, etc.

In present invention, matters relating to genetic engineering technology will be more clear from the contents of Sambrook's literature etc. (Sambrook, et al., Molecular Cloning, A Laboratory Manual, Cold Spring Harbor laboratory Press, Cold Spring Harbor, N.Y. (2001)).

Advantageous Effects

As described in the above, the present invention identified cytokeratin 18 protein as an autoantigen recognized by autoantibodies in the serum samples of patients having COPD. Thus, a pharmaceutical composition of the present invention cytokeratin 18 protein as an active ingredient can be used as a medicament for preventing, alleviating, and treating COPD through the inhibition of autoantibody-induced cytotoxicity to airway epithelial cells and the inhibition of the secondary development of chronic airway epithelial inflammation induced by the formation of immune complexes consisted of autoantibodies and autoantigen.

Also, a diagnostic composition comprising cytokeratin 18 protein according to the present invention can be used for detecting, diagnosing or classifying COPD.

DESCRIPTION OF DRAWINGS

FIG. 1 shows immunoblot analysis of human airway epithelial cell (A549) proteins reacting with IgG autoantibodies in serum samples of healthy controls, pulmonary emphysema patients having normal pulmonary function, and patients with COPD;

FIG. 2 shows immunoblot detection of IgG autoantibodies to recombinant human cytokeratin 18 protein in serum samples of healthy controls, pulmonary emphysema patients with normal pulmonary function, and patients with COPD;

FIG. 3 shows the bindings of IgG autoantibodies in serum samples of COPD with the recombinant human cytokeratin 18 proteins and the commercially available purified bovine cytokeratin 18 protein detected by immunoblot analysis;

FIG. 4 shows the detection of antibody-induced cytotoxicity to human airway epithelial cells (A549) by IgG antibodies purified from serum samples of patients with COPD;

FIG. 5 shows inhibitions of IgG autoantibody-induced cytotoxicity to airway epithelial cells (A549) when the IgG antibodies from patients with COPD were adsorbed with human cytokeratin 18 protein prior to addition to airway epithelial cells;

BEST MODE

Hereinafter, the present invention is more specifically explained by the Examples. However, the following examples are provided for the purpose of illustration and are not intended to limit the scope of the present invention.

EXAMPLE 1

Detection of IgG Autoantibodies to Cytokeratin 18 Protein in Serum Samples from Patients with COPD (1-1) Subjects
Subjects The inventors examined serum samples obtained from 9 patients with chronic obstructive pulmonary disease (COPD), 2 patients with pulmonary emphysema showing normal pulmonary function and 58 healthy controls. Diagnosis of COPD was determined by recently reported criterion of NHLBI/WHO GOLD Workshop summary (Am J Respir Crit. Care Med 2001; 163:1256-1276). Both of 2 patients with pulmonary emphysema had smoking history of more than 10 pack years. They have been clinically complained dyspnea symptom and chest X-ray showed findings compatible with pulmonary emphysema. However, they had normal findings with values of FEV1 (forced expiratory volume in one second) and FVC (forced vital capacity) were greater than 80% of predictive value on pulmonary function test. All 9 patients with COPD had clinical histories compatible with COPD such as cough, sputum, dyspnea, etc. Also, their FEV1 measured following the inhalation of bronchodilator showed less than 80% of predictive value on pulmonary function test, and the ratio of FEV1/FVC was less than 70%. All patients with COPD had smoking history of more than 10 pack years, but had no signs of tuberculosis or other pulmonary diseases in chest X-ray. The serum samples of the patients with COPD were stored at −20° C.

(1-2) Cell Culture

The human airway epithelial cell line A549 (ATCC CCL-185; Giard et al, J Natl Cancer Inst 1973; 51:1417-23) was obtained from American Type Culture Collection (ATTC; VA, USA) and was cultured as recommend by ATCC.

(1-3) Extraction of Cell Proteins and Immunoblot Analysis

Immunoblot analysis was performed with human airway epithelial cells and the serum samples obtained from healthy controls and patients with COPD according to the above Example (1-1), to identify human airway epithelial cell proteins which bind to IgG autoantibodies in the serum.

Firstly, in order to extract proteins from the human airway epithelial cell A549 in the above (1-2), the cultured cells were lysed in lysis buffer containing 10 mM Tris/HCl, pH 7.2, 2% sodium dodecyl sulphate (SDS), 158 mM NaCl, and 10 mM dithiothreitol.

The proteins in cell lysates were separated by discontinuous Sodium Dodecyl Sulfate-PolyacrylAmide Gel Electrophoresis (SDS-PAGE). Following electrophoresis, proteins were transferred onto a polyvinylidine difluoride (PVDF) membrane (Bio-Rad Laboratories, Hercules, Calif.). After the transfer, the PVDF membrane was treated with Tris-buffered saline (TBS) containing 5% bovine serum, 10% powdered skim milk and 0.1% Tween 20 for one or more hours, to block non-specific bindings of proteins to PVDF, and then the PVDF membrane was cut in 4 mm strips. The cut strips were reacted with patients' serum diluted in the same buffer in 1:100 (v/v) for 2 hours at room temperature. After washing, the membrane was incubated with alkaline phosphates-conjugated goat anti-human IgG antibodies (Sigma Chemical Co., St. Louis, Mo.) for 2 hours at room temperature. After the final washing, the membrane was stained with a BCIP/NBT solution (5-bromo-4-chloro-3-indoyl phosphate/nitro blue tetrazolium; Sigma) for 5 minutes to detect the proteins reacted with patients' serum. To compare with results from patients with other disease, a serum sample from a patient with nonallergic asthma that a detection of IgG autoantibodies to cytokeratin 18 has been confirmed by previous report of inventors (Nahm D H, et al. Am J Respir Crit. Care Med 2002; 165:1536-9) was also included in the experiments.

In order to minimize technical errors in detection rate of each test, each test comprised a positive standard serum and negative control serum. The results of the tests were assessed by at least two investigators independently with naked eyes. When test serum showed strong band to certain airway epithelial cell protein compared to negative control serum, the stained intensity of the band were the same as or stronger than that of positive standard serum, and the result read by the two investigators corresponded to each other, which case was defined as the positive detection of autoantibodies.

Mouse monoclonal antibody to cytokeratin 18 protein (clone CK5, Sigma Chemical Co., St. Louis, Mo.), goat antibody to human alpha-enolase protein (Santa Cruz Biotechnology, Santa Cruz, Calif.) and their alkaline phosphatase-conjugated secondary antibodies were included in each experiment to confirm the location of the reacting autoantigen proteins when the detection results of the autoantibodies to airway epithelial cell proteins were read.

The target autoantigen protein was determined by comparing and analyzing the results of immunoblot localization of airway epithelial cell proteins on the PVDF membrane reacting with IgG autoantibodies of patients and airway epithelial cell proteins reacting with mouse monoclonal antibody to cytokeratin 18 protein (clone CK5, Sigma Chemical Co., St. Louis, Mo.) or goat antibody to human alpha-enolase protein (Santa Cruz Biotechnology, Santa Cruz, Calif.) in the points of staining patterns and molecular weights.

FIG. 1 shows result of immunoblot analysis of airway epithelial cell (A549) proteins reacting with IgG autoantibodies in serum samples of healthy controls, patients with pulmonary emphysema showing normal pulmonary function, and patients with COPD. Lanes 1 and 2 show the results for serum samples of healthy controls, lanes 3 and 4 show the results for serum samples of patients with pulmonary emphysema showing normal pulmonary function, lanes 5-13 show the results for serum samples of patients with COPD, and lane 14 shows the result for a serum sample of a patient with bronchial asthma, lane 15 shows the result for mouse monoclonal antibodies to cytokeratin 18 protein, and lane 16 shows the result for goat antibodies to alpha-enolase.

FIG. 1 shows that IgG autoantibodies to protein band corresponding to cytokeratin 18 protein identified by mouse monoclonal antibodies were detected in 8 (89%) of total 9 patients with chronic obstructive pulmonary disease. This result showed significantly higher detection rate than that of healthy controls (5 of 58 healthy control; 8.6%) (chi-square test, $p<0.05$).

(1-4) Detection of Autoantibodies in the Blood Samples of Patients with COPD Using Recombinant Human Cytokeratin 18 Protein By using the above subjects' serum of (1-3) and commercially available human recombinant cytokeratin 18 protein (Research Diagnostics INC., Pleasant Hill Road Flanders, N.J.) produced from *E. Coli* by the genetic engineering technology, immunoblot was performed in same sample arrangement as in FIG. 1. The results are shown in FIG. 2.

FIG. 2 shows immunoblot detection of IgG autoantibodies to recombinant human cytokeratin 18 protein using serum samples of healthy controls, patients with pulmonary emphysema showing normal pulmonary function, and patients with COPD. Lanes 1 and 2 show the results for serum samples of healthy controls, lanes 3 and 4 show the results for serum samples of patients with pulmonary emphysema showing normal pulmonary function, lanes 5-13 show the results for serum samples of patients with COPD, and lane 14 shows the result for a serum sample of a patient with bronchial asthma, lane 15 shows the result for mouse monoclonal antibodies to cytokeratin 18 protein, and lane 16 shows the result for goat antibodies to alpha-enolase.

As shown in FIG. 2, IgG autoantibodies to recombinant human cytokeratin 18 protein were clearly detected in 3 (33.3%) of 9 patients with COPD (lanes 7, 11, and 13)., IgG autoantibodies to recombinant human cytokeratin 18 protein were also detected in other 5 patients with COPD (lanes 5, 6, 8, 9, 10 in FIG. 2) and two patients with pulmonary emphysema showing normal pulmonary function (lane 3, 4 in FIG. 2).

As the results of FIG. 2 were consistent with the results of FIG. 1, it was confirmed that the autoantigen reacting with IgG autoantibodies in serum samples from patients with COPD was human cytokeratin 18 protein.

As shown in FIG. 1 and FIG. 2, IgG autoantibodies to recombinant cytokeratin 18 protein or cytokeratin 18 protein in airway epithelial cells were positively detected in patients with COPD.

Thus, it was reconfirmed that the autoantigen reacting with IgG autoantibodies in the serum samples of patients with COPD was cytokeratin 18 protein (FIG. 2).

EXAMPLE 2

Immunoblot Analysis for Bovine Cytokeratin 18 Protein

In order to determine whether IgG autoantibodies in serum samples of patients with COPD are selectively reacted with human cytokeratin 18 protein or they could react with cytokeratin 18 proteins from other mammal, the inventors performed immunoblot analysis.

Reaction of IgG autoantibodies in serum samples from 3 patients with COPD with commercially available recombinant human cytokeratin 18 protein and purified bovine cytokeratin 18 protein (Research Diagnostics INC., Pleasant Hill Road Flanders, N.J.) was detected and compared by immunoblot analysis, according to the method of (1-3). The results are shown in FIG. 3.

FIG. 3 shows immunoblot results that show comparing the reaction of IgG autoantibodies in serum samples of patients with COPD with recombinant human cytokeratin 18 protein and purified bovine cytokeratin 18 protein. Lanes 1, 3, 5 and 7 show the results of the recombinant human cytokeratin 18 protein, and lanes 2, 4, 6, and 8 show the results of purified bovine cytokeratin 18 protein. Lanes 1 & 2, lanes 3 & 4, and lanes 5 & 6 show the results obtained by reacting with 3 serum samples of 3 patients with COPD, and lanes 7 & 8 show the result of reacting with mouse monoclonal antibodies to cytokeratin 18 protein.

From the results obtained by using the serum samples of 3 patients with COPD, it was confirmed that IgG autoantibodies to cytokeratin 18 in their serum samples could react with bovine cytokeratin 18 protein having the same molecular weight of human cytokeratin 18 protein.

As shown in the above, the test results of autoantigen-autoantibodies using human recombinant human cytokeratin 18 protein and purified bovine cytokeratin 18 protein corresponded to each other. Thus, it was confirmed that bovine cytokeratin 18 protein could be used to detect autoantibody in serum samples of patients with COPD.

EXAMPLE 3

Inhibition of IgG Antibody-induced Cytotoxicity to Airway Epithelial Cells by the Administration of Cytokeratin 18 Protein (3-1) Confirmation of Cytotoxicity to Airway Epithelial Cells by IgG Autoantibodies Cytotoxicity to airway epithelial cell by IgG autoantibodies was measured by the microcytotoxicity method using Terasaki tray and modifying prior reported method (Martin S, et al; Tissue Antigens 1991; 37:152-155).

In the above test, IgG antibodies were isolated from plasma samples of 2 patients with COPD, and a healthy control, where patients with COPD had IgG autoantibodies to human cytokeratin 18 protein.

IgG antibodies of 1 healthy control were isolated to have a purity of 90%, by using ethanol precipitation and ultrafiltration according to prior preparing method of IgG antibodies (Lebing W et al, Vox Sang 2003; 84:193-201). IgG antibodies of 2 patients with COPD were isolated in purity of greater than 95% by affinity chromatography using Protein A column. The purity of the isolated IgG antibodies was determined by SDS-PAGE and protein staining. Also, the amount of endotoxin in the isolated IgG antibody solution was measured quantitatively by using LAL (*Limulus amebocyte lysate*). As a result, the contamination of endotoxin was not detected.

Human IgG antibodies used for intravenous administration (IVglobulin, Green Cross Pharmaceutical Co., Korea) were commercially obtained and used as control IgG antibodies, where the control IgG antibodies were isolated from plasma of a large number of blood donors, to have a purity of more than 95%.

First of all, the above human IgG antibodies were diluted by using DMEM/F12 medium at concentrations of 5 mg/ml, 1 mg/ml, and 0.2 mg/ml. Then, the diluted samples were put into 96-well Terasaki tray at a ratio of 1 μl/well in quadruplicate. Also, samples containing only DMEM/F12 medium were put in 96-well Terasaki tray in quadruplicate as negative controls.

The cultured human airway epithelial cell line A549 was treated with Trypsin/EDTA and isolated, then 1 μl (2000 cells/μl) of the solution was put into each of above wells. In order to prevent evaporation of the solution, 5 μl of mineral oil was put into the wells. And then, the wells were reacted for 2 hours and 30 minutes. 5% eosin Y dye (Sigma Chemical Co.) was put into the wells at a ratio of 5 μl/well to stain the cells. Then, formalin solution was put into the wells at a ratio of 5 μl/well to fix the stained cells. A coverslide was covered and the number of cells without damage of cell membrane was counted by light microscope to determine cytotoxicity.

The cytotoxicity to airway epithelial cell by IgG antibodies was expressed as cytolysis % according to following equation, by comparing mean number of cells in wells reacting with the samples and mean number of cells in negative control wells containing only DMEM/F12 medium.

Cytotoxicity (cytolysis %)=[(mean number of cells in negative control wells−mean number of cells in wells containing samples)/mean number of cells in negative control wells]×100    [Equation 1]

The result of the test was obtained in quadruplicate to each sample, and then expressed in terms of mean and standard deviation.

FIG. 4 show that IgG antibodies isolated from plasma samples of 2 patients with COPD (patient 1 and patient 2) show significantly higher cytotoxicity than commercial IgG antibodies obtained from multiple healthy donors used for intravenous administration (IVglobulin; normal controls 1) or IgG antibodies isolated from plasma of a healthy control (normal control 2) under the conditions of 1 μg/well and 5 μg/well (t-test, p<0.05).

(3-2) Inhibition of IgG Autoantibody-Induced Cytotoxicity to Airway Epithelial Cell by Cytokeratin 18 Protein In order to absorb autoantibodies to cytokeratin 18 protein from patients with COPD, 50 μg of the human cytokeratin 18 protein purified according to the previous report of the inventors (Nahm D H, et al. Am J Respir Crit. Care Med 2002; 165:1536-9) and 50 μg of the purified human cytokeratin 19 protein as a negative control were subjected to electrophoresis and transferred to PVDF membrane. PVDF membranes containing human cytokeratin 18 protein or human cytokeratin 19 protein were cut into small pieces and transferred to eppendorf tubes separately.

50 μg of IgG antibodies which were isolated from serum samples of 2 patients with COPD and diluted in DMEM/F12 medium to have a concentration of 5 mg/ml were mixed with PVDF membrane pieces containing either 50 μg of human cytokeratin 18 protein or human cytokeratin 19 protein, and then, the mixtures were reacted for 16 hours at 4° C. After the reaction, supernatant was collected by centrifugation, and the cytotoxicity to human airway epithelial cell by IgG antibodies was measured in the above method (3-1).

The result of the experiment was obtained in 6 independent experiments of each samples, and then, expressed in terms of mean and standard deviation.

FIG. 5 shows that when the IgG antibodies of patients with COPD (patient 1, 2) were adsorbed with human cytokeratin 18 protein prior to the addition to airway epithelial cells, the cytotoxicity to airway epithelial cell by IgG autoantibodies (shown as "CK18" in each graph) was significantly reduced compared to the case of adsorbtion with the same amount of human cytokeratin 19 protein used as a control antigen (shown as "CK19" in each graph) (Table 1) (t-test, p<0.001).

TABLE 1

| Patients | Absorption with cytokeratin 19 protein (cytolysis %) | Absorption with cytokeratin 18 protein (cytolysis %) |
| --- | --- | --- |
| Patient 1 | 61.9 ± 6.4* | 13.7 ± 4.5 |
| Patient 2 | 37.2 ± 6.2* | 1.8 ± 2.7 |

*P < 0.01

Above results show that cytokeratin 18 protein can be used for the inhibition of cytotoxic reaction to airway epithelial cell induced by IgG autoantibodies to cytokeratin 18 protein in the blood of patients with COPD.

Accordingly, it is evident that the cytotoxic effect and the inflammatory effect of IgG autoantibodies can be repressed if the cytokeratin 18 protein of the present invention is administered into the patients with COPD.

INDUSTRIAL APPLICABILITY

As described in the above, the present invention identified cytokeratin 18 protein as an autoantigen recognized by autoantibodies in the serum samples of patients having COPD. Thus, a pharmaceutical composition of the present invention cytokeratin 18 protein as an active ingredient can be used as a medicament for preventing, alleviating, and treating COPD through the inhibition of autoantibody-induced cytotoxicity to airway epithelial cells and the inhibition of the secondary development of chronic airway epithelial inflammation induced by the formation of immune complexes consisted of autoantibodies and autoantigen.

Also, a diagnostic composition comprising cytokeratin 18 protein according to the present invention can be used for detecting, diagnosing or classifying COPD.

Also, the present invention can be used for a pharmaceutical formulation comprising cytokeratin 18 protein or fragments thereof to protect patients with COPD. The present invention also can be used to identify a pharmaceutical compound capable of inhibiting the binding ability of autoantibodies to cytokeratin 18 from patients with COPD to cytokeratin 18 protein or cytokeratin 18-expressing cells.

What is claimed is:

1. A method to aid in the detection of chronic obstructive pulmonary disease in a human subject, comprising the steps of:
   (a) obtaining a biological sample from the human subject;
   (b) contacting the biological sample with human cytokeratin 18 protein to form an immune complex between the human cytokeratin 18 protein and autoantibodies in the biological sample; and
   (c) determining the presence of the autoantibodies against the human cytokeratin 18 protein in the biological sample by detecting the immune complex, wherein the presence of the autoantibodies bears a positive correlation with the existence of chronic obstructive pulmonary disease in the human subject.

2. The method of claim 1, wherein the cytokeratin 18 protein has the amino acid sequence of SEQ ID NO: 1.

3. The method of claim 1, wherein the chronic obstructive pulmonary disease is pulmonary emphysema or chronic bronchitis.

4. The method of claim 1, wherein said biological sample is selected from the group consisting of blood, plasma, serum, urine, tears, and saliva.

5. The method of claim 1, wherein said biological sample is serum.

6. The method of claim 1, wherein the chronic obstructive pulmonary disease is pulmonary emphysema.

7. The method of claim 1, wherein the chronic obstructive pulmonary disease is chronic bronchitis.

8. A method to aid in the detection of chronic obstructive pulmonary disease (COPD) in a human subject, comprising the steps of:
   (a) contacting a biological sample from a subject suspected to have chronic obstructive pulmonary disease with cytokeratin 18 protein to induce the formation of immune complex; and
   (c) detecting the presence of the immune complex, wherein the presence of the immune complex bears a positive correlation with the existence of chronic obstructive pulmonary disease in the human subject.

9. The method of claim 8, wherein the cytokeratin 18 protein is originated from a mammal selected from the group consisting of human, mouse, rat, rabbit, pig, cow and goat.

10. The method of claim 8, wherein the cytokeratin 18 protein has the amino acid sequence of SEQ ID NO: 1.

11. The method of claim 8, wherein the cytokeratin 18 protein has the amino acid sequence of SEQ ID NO: 2.

12. The method of claim 8, wherein the chronic obstructive pulmonary disease is pulmonary emphysema.

13. The method of claim 8, wherein the chronic obstructive pulmonary disease is chronic bronchitis.

14. The method of claim 8, wherein said biological sample is selected from the group consisting of blood, plasma, serum, urine, tears, and saliva.

15. The method of claim 8, wherein said biological sample is serum.

* * * * *

UNITED STATES PATENT AND TRADEMARK OFFICE
CERTIFICATE OF CORRECTION

PATENT NO. : 7,981,619 B2  Page 1 of 1
APPLICATION NO. : 11/883589
DATED : July 19, 2011
INVENTOR(S) : Sook-yeong Jeon et al.

It is certified that error appears in the above-identified patent and that said Letters Patent is hereby corrected as shown below:

Claim 8, column 20, line 45, change "(c)" to --(b)--.

Signed and Sealed this
Fourth Day of October, 2011

David J. Kappos
*Director of the United States Patent and Trademark Office*